(12) United States Patent
Bydlon et al.

(10) Patent No.: US 11,857,268 B2
(45) Date of Patent: Jan. 2, 2024

(54) OPTICAL SHAPE SENSING DEVICE WITH INTEGRATED FORCE SENSING REGION AND TIP INTEGRATION

(71) Applicant: KONINKLIJKE PHILIPS N.V., Eindhoven (NL)

(72) Inventors: Torre Michelle Bydlon, Melrose, MA (US); Alexandru Patriciu, Belmont, MA (US); Marcin Arkadiusz Balicki, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 661 days.

(21) Appl. No.: 17/051,945

(22) PCT Filed: Apr. 23, 2019

(86) PCT No.: PCT/EP2019/060259
§ 371 (c)(1),
(2) Date: Oct. 30, 2020

(87) PCT Pub. No.: WO2019/211112
PCT Pub. Date: Nov. 7, 2019

(65) Prior Publication Data
US 2021/0113274 A1 Apr. 22, 2021

Related U.S. Application Data

(60) Provisional application No. 62/665,583, filed on May 2, 2018.

(51) Int. Cl.
*G01N 21/00* (2006.01)
*A61B 34/20* (2016.01)
(Continued)

(52) U.S. Cl.
CPC .............. *A61B 34/20* (2016.02); *G01B 11/24* (2013.01); *G01L 1/246* (2013.01); *A61B 2034/2061* (2016.02); *A61B 2090/064* (2016.02)

(58) Field of Classification Search
CPC ............ A61B 34/20; A61B 2034/2061; A61B 2090/064; G01B 11/24; G01L 1/246
See application file for complete search history.

(56) References Cited

U.S. PATENT DOCUMENTS 7,772,541 B2  8/2010  Froggatt
8,347,738 B2  1/2013  Tung
(Continued)

FOREIGN PATENT DOCUMENTS

EP   2363073      9/2011
WO   2012095760   7/2012
WO   2013/150019  10/2013

OTHER PUBLICATIONS

International Search Report and Written Opinion dated Sep. 23, 2019 for International Application No. PCT/EP2019/060259 Filed Apr. 23, 2019.
(Continued)

*Primary Examiner* — Abdullahi Nur

(57) ABSTRACT

An optical shape sensing device includes an elongated outer body with flexible tubing configured to maneuver through a passage; a multicore optical fiber extending through the elongated outer body, and enabling shape sensing by tracking deformation of the multicore optical fiber along a length of the multicore optical fiber; a termination piece attached to a distal tip of the multicore optical fiber, the termination piece having a distal tip; and a force sensing region integrated with the elongated outer body and configured to enable determining of an axial force exerted on a distal end
(Continued)

of the elongated outer body. The shape sensing occurs along the multicore optical fiber to the distal tip of the termination piece.

21 Claims, 8 Drawing Sheets

(51) Int. Cl.
*G01B 11/24* (2006.01)
*G01L 1/24* (2006.01)
*A61B 90/00* (2016.01)

(56) References Cited

U.S. PATENT DOCUMENTS

| | | | | |
|---|---|---|---|---|
| 8,773,650 | B2* | 7/2014 | Froggatt | G01L 1/242 |
| | | | | 356/73.1 |
| 8,811,777 | B2* | 8/2014 | Younge | A61B 1/009 |
| | | | | 385/13 |
| 9,429,696 | B2* | 8/2016 | Donhowe | A61B 34/30 |
| 2009/0177095 | A1* | 7/2009 | Aeby | A61M 25/00 |
| | | | | 600/478 |
| 2010/0332030 | A1 | 12/2010 | Larkin | |
| 2011/0087112 | A1 | 4/2011 | Leo | |
| 2017/0196479 | A1 | 7/2017 | Liu | |
| 2018/0161119 | A1* | 6/2018 | Ruppersberg | A61B 5/6852 |

OTHER PUBLICATIONS

Abushagur, et al, "Advances in Bio-Tactile Sensors for Minimally Invasive Surgery Using the Fibre Bragg Grating Force Sensor Technique: A Survey", Sensors (Basel). Apr. 9, 2014; 14(4): 6633-65.
Ho, et al, "FBG Sensor for Contact Level Monitoring and Prediction of Perforation in Cardiac Ablation", Sensors (Basel). 2012;12(1):1002-13.
Liu, et al, "Miniature fiber-optic force sensor based on low-coherence Fabry-Pérot interferometry for vitreoretinal microsurgery", Biomed Opt Express. May 1, 2012;3(5):1062-76.
He, et al, "A Sub-Millimetric 3-DOF Force Sensing Instrument with Integrated Fiber Bragg Grating for Retinal Microsurgery", IEEE Trans Biomed Eng. Feb. 2014;61(2):522-34.

* cited by examiner

OPTICAL SHAPE SENSING DEVICE WITH INTEGRATED FORCE SENSING REGION AND TIP INTEGRATION

CROSS REFERENCE TO RELATED APPLICATIONS

This application is the U.S. National Phase application under 35 U.S.C. § 371 of International Application No. PCT/EP2019/060259 filed Apr. 23, 2019, which claims the benefit of U.S. Provisional Patent Application No. 62/665,583 filed May 2, 2018. These applications are hereby incorporated by reference herein.

TECHNICAL FIELD

This disclosure relates to optical shape sensing (OSS) devices, e.g., used for minimally invasive medical procedures, and more particularly to OSS devices including multicore optical fiber extending longitudinally through an elongated outer body, a termination piece attached to a distal tip of the multicore optical fiber, and a force sensing region integrated with the elongated outer body. Shape sensing thus occurs along the entire length of the multicore optical fiber to its distal tip, and is further projected to a distal tip of the termination piece, while the termination piece is protected against breakage caused by excessive axial and other forces.

BACKGROUND

OSS devices use light along a multicore optical fiber for device localization and navigation during surgical intervention, for example. Generally, distributed strain measurements in the optical fiber are made using characteristic Rayleigh backscatter or controlled grating patterns. The shape along the optical fiber begins at a specific point along the sensor, known as the launch or z=0. Subsequent shape position and orientation of the body of the OSS device are determined relative to that point.

The multicore optical fibers may be integrated into medical OSS devices in order to provide live guidance of the devices during minimally invasive procedures, which reduce discomfort and recovery time of a patient. The integrated, multicore optical fibers provide position and orientation information of the entire OSS device, including the shape of the OSS device. For example, an OSS device may include a shape-sensed guidewire or shape-sensed catheter used for navigation to a renal artery, with the guidance information being overlaid on a pre-operative computer tomography (CT) image.

Notably, the multicore optical fibers contain more information than just position and orientation of the OSS device. For example, axial strain on the optical fibers may be used to determine how much force is applied to the tip of the OSS device via the compression (or tension) of fiber Bragg gratings (FBGs), which are useful for sensing axial forces in small OSS devices. However, some OSS devices are unique in that the optical fibers have a termination piece which cannot tolerate axial forces (e.g., above predefined thresholds) applied to them without breaking.

Accordingly, there is a need to integrate multicore optical fiber of an OSS device with a termination piece at the end to be able to shape sense the OSS device all the way to the tip of the termination piece, while simultaneously being able to measure forces applied to the end of the OSS device without risk of termination piece or optical fiber breakage.

SUMMARY

According to illustrative embodiment, an OSS device includes an elongated outer body with flexible tubing configured to maneuver through a passage; a multicore optical fiber extending through the elongated outer body, and enabling shape sensing by tracking deformation of the multicore optical fiber along a length of the multicore optical fiber; a termination piece attached to a distal tip of the multicore optical fiber, the termination piece having a distal tip; and a force sensing region integrated with the elongated outer body and configured to enable determining of an axial force exerted on a distal end of the elongated outer body. The shape sensing occurs along the multicore optical fiber to the distal tip of the termination piece.

BRIEF DESCRIPTION OF THE DRAWINGS

The present invention will be more readily understood from the detailed description of exemplary embodiments presented below considered in conjunction with the accompanying drawings, as follows.

DETAILED DESCRIPTION

Figure 1:
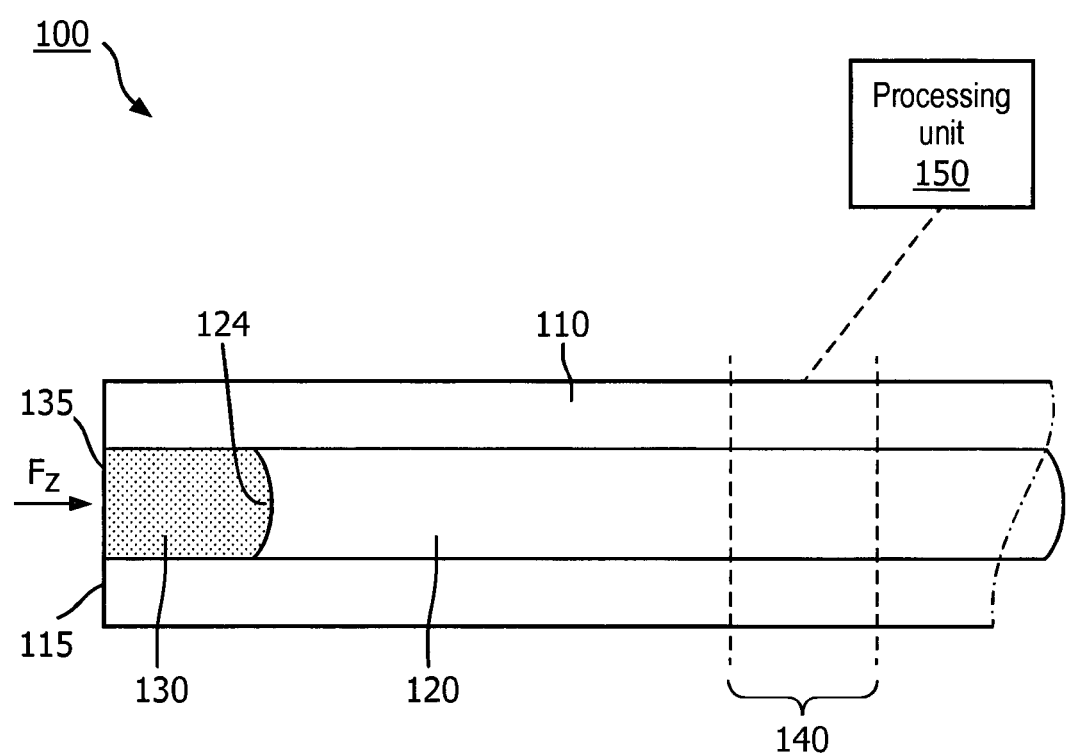
FIG. 1 is a simplified cross-sectional diagram of an optical shape sensing device including a force sensing region, according to a representative embodiment.

The present invention will now be described more fully hereinafter with reference to the accompanying drawings, in which embodiments of the present invention are shown.

The present invention may, however, be embodied in different forms and should not be construed as limited to the embodiments set forth herein. Rather, these embodiments are provided as teaching examples of the invention.

Generally, FBGs may be integrated into OSS devices for force sensing. That is, FBGs can be used to measure axial strain in an optical fiber, where axial strain is a measure of temperature changes and axial force. When temperature is decoupled from the measurement, axial strain can be used to determine the axial force applied to the optical fiber; or if multiple FBGs are located along the length of an optical fiber, the shape of the optical fiber may be determined. At positions between FBGs or beyond the tip of the optical fiber, the shape can be estimated, projected, averaged, or the like. In multicore optical fiber with FBGs along the entire length of the optical fiber, signal losses at the distal tip of the optical fiber can obscure the FBG signals, diminishing shape sensing quality at the distal tip. A termination piece that is bound to a multicore optical fiber improves signal quality at the distal tip of the multicore optical fiber, thereby permitting shape sensing to be performed all the way to the distal tip of the multicore optical fiber. The term "shape sensing" used herein includes estimation, projection, and averaging of shape beyond the optical fiber, particularly with regard to projecting shape to a distal tip of the termination piece. The shape of the termination piece, or the remainder of the distal OSS device (the end of which may substantially correspond to the distal tip of the termination piece), may be determined in various ways, such as projecting the shape in a straight line from the distal tip of the multicore optical fiber to the distal tip of the termination piece.

The termination piece may be broken by sufficient forces applied to the distal tip, in which case shape sensing to the distal end of the corresponding OSS device cannot be done simultaneously with measuring applied axial forces. Therefore, according to various embodiments, force sensing is enabled using a multicore optical fiber (e.g., of a guidewire or other OSS device) and a termination piece attached thereto, without breaking the termination piece while being able to shape sense all the way to the tip of the termination piece or the OSS device. Also, flexibility sufficient to navigate the OSS device through small spaces or passages is maintained.

According to a representative embodiment, an OSS device includes an elongated outer body comprising flexible tubing configured to maneuver through a passage; an optical fiber extending through the elongated outer body, and enabling shape sensing by tracking deformation of the optical fiber along a length of the optical fiber; a termination piece attached to a distal tip of the optical fiber, the termination piece comprising a distal tip; and a force sensing region integrated with the elongated outer body and configured to sense an axial force exerted on a distal end of the elongated outer body via changes in axial strain on the optical fiber. The shape sensing occurs along the optical fiber to the distal tip of the termination piece.

It should be understood that the disclosure is provided in terms of medical instruments; however, the present teachings are much broader and are applicable to any imaging instruments and imaging modalities. In some embodiments, the present principles are employed in tracking or analyzing complex biological or mechanical systems. In particular, the present principles are applicable to internal tracking procedures of biological systems and procedures in all areas of the body such as the lungs, gastro-intestinal tract, excretory organs, blood vessels, etc. The elements depicted in the figures may be implemented in various combinations of hardware and software and provide functions which may be combined in a single element or multiple elements.

It should be further understood that the terminology used herein is for purposes of describing particular embodiments only, and is not intended to be limiting. Any defined terms are in addition to the technical and scientific meanings of the defined terms as commonly understood and accepted in the technical field of the present teachings.

As used in the specification and appended claims, the terms "a", "an" and "the" include both singular and plural referents, unless the context clearly dictates otherwise. Thus, for example, "a device" includes one device and plural devices. The statement that two or more parts or components are "coupled" shall mean that the parts are joined or operate together either directly or indirectly, i.e., through one or more intermediate parts or components, so long as a link occurs.

Directional terms/phrases and relative terms/phrases may be used to describe the various elements' relationships to one another, as illustrated in the accompanying drawings. These terms/phrases are intended to encompass different orientations of the device and/or elements in addition to the orientation depicted in the drawings.

A "computer-readable storage medium" encompasses any tangible storage medium which may store instructions which are executable by a processor of a computing device. The computer-readable storage medium may be referred to as a non-transitory computer-readable storage medium, to distinguish from transitory media such as transitory propagating signals. The computer-readable storage medium may also be referred to as a tangible computer-readable medium.

In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, data may be retrieved over a modem, over the internet, or over a local area network. References to a computer-readable storage medium should be interpreted as possibly being multiple computer-readable storage mediums. Various executable components of a program or programs may be stored in different locations. The computer-readable storage medium may for instance be multiple computer-readable storage medium within the same computer system. The computer-readable storage medium may also be computer-readable storage medium distributed amongst multiple computer systems or computing devices.

"Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa. References to "computer storage" or "storage" should be interpreted as possibly including multiple storage devices or components. For instance, the storage may include multiple storage devices within the same computer system or computing device. The storage may also include multiple storages distributed amongst multiple computer systems or computing devices.

A "processor" as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have instructions performed by multiple processors that may be within the same computing device or which may even be distributed across multiple computing devices.

A "processing unit" as used herein encompasses one or more processors, computers, application specific integrated circuits (ASICs), field-programmable gate arrays (FPGAs), or combinations thereof, using software, firmware, hard-wired logic circuits, or combinations thereof. That is, a processing unit may be constructed of any combination of hardware, firmware or software architectures, and may include its own memory (e.g., nonvolatile memory), computer-readable storage medium and/or computer storage for storing executable software/firmware executable code and/or data that allows it to perform the various functions. In an embodiment, processing unit may include a central processing unit (CPU), for example, executing an operating system.

A "user interface" or "user input device" as used herein is an interface which allows a user or operator to interact with a computer or processing unit (computer system). A user interface may provide information or data to the operator and/or receive information or data from the operator. A user interface may enable input from an operator to be received by the computer and may provide output to the user from the computer. In other words, the user interface may allow an operator to control or manipulate a computer system and the interface may allow the computer system indicate the effects of the user's control or manipulation. The display of data or information on a display or a graphical user interface is an example of providing information to an operator. The receiving of data through a touch screen, keyboard, mouse, trackball, touchpad, pointing stick, graphics tablet, joystick, gamepad, webcam, headset, gear sticks, steering wheel, wired glove, wireless remote control, and accelerometer are all examples of user interface components which enable the receiving of information or data from a user.

A "hardware interface" encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A "display" or "display device" or "display unit" as used herein encompasses an output device or a user interface adapted for displaying images or data, e.g., from a computer system. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Multiple, illustrative embodiments of an OSS device which integrates optical fiber and a termination piece into a structure that enables force sensing via changes in axial strain. The embodiments are intended to be illustrative, and not exhaustive, such that the additional related configurations may be included. In all of the embodiments, the termination piece of the optical fiber is protected from axial forces being applied directly to a tip of the termination piece. As discussed above, direct axial force on the termination piece can cause the termination piece or the multicore optical fiber to break, and thereby prevent shape sensing of the OSS device all the way to the distal end. Throughout the disclosure, like numbered elements in these figures are either equivalent elements or perform the same function. Elements which have been discussed previously will not necessarily be discussed in later figures if the function is equivalent.

FIG. 1 is a simplified cross-sectional diagram of an optical shape sensing device including a force sensing region, according to a representative embodiment.

Referring to FIG. 1, optical shape sensing device 100 is an elongated, primarily flexible device configured for navigation through narrow passages, although rigid portion(s) may be included for purposes of measuring axial force $F_z$, as discussed below. For example, the optical shape sensing device 100 may be configured as a shape-sensed guidewire or catheter used for navigation through vasculature of a patient during interventional medical procedures, although other configurations and/or uses may be incorporated without departing from the scope of the present teachings.

In the depicted embodiment, the optical shape sensing device 100 includes an elongated outer body 110, which includes flexible tubing, e.g., to enable maneuvering of the optical shape sensing device 100 through a passage, as discussed above. The optical shape sensing device 100 also includes a multicore optical fiber 120 extending longitudinally through the elongated outer body 110, and a termination piece 130 attached to a distal tip 124 of the multicore optical fiber 120. The termination piece 130 includes a distal tip 135, which may substantially coincide with a distal end 115 of the elongated outer body 110 (as well as the distal end of the optical shape sensing device 100).

Since the termination piece 130 is bound to the mutlicore optical fiber 120, shape sensing is enabled by the optical shape sensing device 100 along the length of the multicore optical fiber 120 and to the distal tip 135 of the termination piece 130. As discussed above, this means that optical fiber shape sensing is performed to the distal tip 124 of the multicore optical fiber 120 and projected to the distal tip 135 of the termination piece 130 (collectively referred to as shape sensing). A typical conventional optical shape sensing device differs in that, without a termination piece, good shape sensing data cannot be obtained even to the distal tip of the multicore optical fiber. Also, there is a risk of breakage, since conventional optical shape sensing devices do not include termination pieces, and/or the termination pieces cannot tolerate axial forces, as discussed above. Generally, the multicore optical fiber 120 may include a central optical core and at least two additional optical cores (not shown) helically wrapped around the central optical core, as would be apparent to one of ordinary skill in the art. The multicore optical fiber 120 enables shape sensing by tracking deformation along its length.

The optical shape sensing device 100 further includes a force sensing region 140 integrated with the elongated outer body 110. The force sensing region 140, together with a processing unit 150, is configured to sense an amount of axial force exerted on the distal end 115 of the elongated outer body 110. In various configurations, the amount of axial force exerted on the distal end 115 may be determined by measuring changes in axial strain on the multicore optical fiber 120 at the force sensing region 140, or by measuring torsion (twist) of the helically wrapped optical fibers of multicore optical fiber 120 at the force sensing region 140, although other types of measurements may be incorporated without departing from the scope of the present teachings. The amount axial force exerted on the distal end 115 of the elongated outer body 110 is determined by the processing unit 150, for example, which applies the axial strain measurement and/or the torsion measurement received from the force sensing region 140 to corresponding known algorithms.

The axial strain, in particular, measured using the multicore optical fiber 120 is directly related to temperature changes and forces applied to the multicore optical fiber 120. When constant temperature is assumed, then the measured axial strain on the central optical fiber is proportional to the axial force on the distal end 115 of the elongated outer body 110. FBGs are well known to be capable of measuring forces exerted on FBG enabled devices in biological settings, for example. Usage of guidewires or other interventional instruments, configured according to various embodiments of the disclosure to measure axial forces for cardiovascular procedures, for example, such as chronic total occlusion (CTO) crossings, confirming tissue contact for ablations in the heart, transeptal puncture, and vessel wall interactions, helps to prevent tissue damage, since the amount of axial force being applied is accurately determined.

Figure 2:
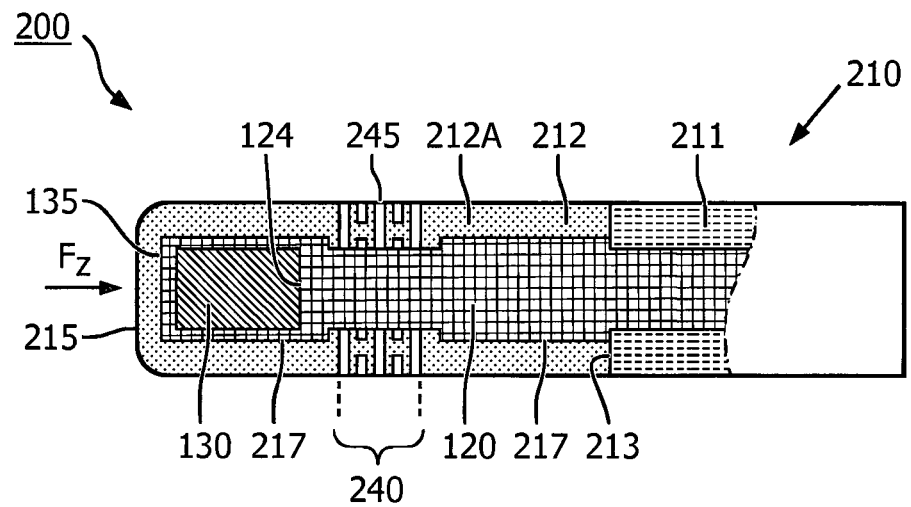
FIG. 2 is a simplified schematic diagram of a cut-away view of an optical shape sensing device including a force sensing region, according to a representative embodiment.

FIG. 2 is a simplified schematic diagram of a cut-away view of an optical shape sensing device including a force sensing region, according to a representative embodiment.

Referring to FIG. 2, optical shape sensing device 200 includes an elongated outer body 210, which includes flexible tubing 211 and rigid tube 212 attached to the flexible tubing 211. In the depicted embodiment, the rigid tube 212 is attached to a distal end 213 of the flexible tubing 211. The flexible tubing 211 enables the maneuvering of the optical shape sensing device 200 through a passage, as discussed above. The flexible tubing 211 may be formed of various flexible materials, such as polyethylene, polyether ether ketone, polypropylene, nylon, polyimide, acetal or acrylonitrile butadiene styrene, and the rigid tube 212 may be formed of various less flexible materials, such as nitinol, stainless steel, titanium, aluminum, and various metal or plastics, such as polyether ether ketone, polypropylene, nylon, polyimide, acetal, and acrylonitrile butadiene styrene, although different materials may be incorporated without departing from the scope of the present teachings.

The optical shape sensing device 200 also includes multicore optical fiber 120 extending longitudinally through the elongated outer body 210, and a termination piece 130 attached to a distal tip 124 of the multicore optical fiber 120, as discussed above. The termination piece 130 is positioned within the rigid tube 212, and includes the distal tip 135, which may substantially coincide with a distal end 215 of the elongated outer body 210. Shape sensing is enabled by the optical shape sensing device 200 along the multicore optical fiber 120 to the distal tip 135 of the termination piece 130.

The optical shape sensing device 200 further includes a force sensing region 240 integrated with the elongated outer body 210. For example, the rigid tube 212 may be micromachined to have a proximal rigid section 212A, a distal rigid section 212B, and a middle elastic segment 245 located in between. Thus, the elastic segment 245 is located proximally from the termination piece 130. In the depicted embodiment, the force sensing region 240 of the optical shape sensing device 200 coincides with the elastic segment 245. The elastic segment 245 enables axial compression and expansion of the rigid tube 212 of the elongated outer body 210 responsive to an axial force $F_z$ exerted on the distal end 215 of the elongated body 210.

Adhesive 217 binds the multicore optical fiber 120 to an inner surface of both the proximal rigid section 212A of the rigid tube 212 (at a proximal side of the elastic segment 245), and the distal rigid section 212B of the rigid tube 212 (at a distal side of the elastic segment 245). The adhesive 217 also binds the multicore optical fiber 120 to an inner surface of the termination piece 130 in the distal rigid section 212B. The adhesive 217 may be an epoxy or an anaerobic adhesive material, for example, although different materials may be incorporated without departing from the scope of the present teachings.

The design of the elastic segment 245 dictates the degree to which the optical shape sensing device 200 compresses or bends. In the depicted embodiment the elastic segment 245 comprises a pattern of slits formed around an outer circumference of the rigid tube 212. The pattern of slits may be formed in the rigid tube 212 by 3D printing, laser cutting, micro-machining, casting, or lithographic techniques, for example, although other slit formation techniques may be incorporated without departing from the scope of the present teachings. Also, the pattern of slits may be formed prior to attachment of the rigid tube 212 to the flexible tubing 211. In alternative embodiments, the elastic segment 245 may comprise other types of flexible structures, such as a laser cut design (not shown) formed around the outer circumference of the rigid tube 212, or a coil spring, as discussed below with reference to FIGS. 6 and 7, for example.

The force sensing region 240, together with the processing unit 150 (not shown in FIG. 2), is configured to sense the amount of axial force exerted on the distal end 215 of the elongated outer body 210, which corresponds to the distal end of the rigid tube 212. When the elastic segment 245 compresses, the bare (without adhesive 217) multicore optical fiber 120 between the proximal and distal rigid sections 212A and 212B also compresses, and the axial strain in this area is used to calculate the applied force. Determination of the amount of axial force exerted on the distal end 215 involves measuring changes in axial strain on the central optical fiber of the multicore optical fiber 120 at the force sensing region 240, as discussed above.

Figure 3:
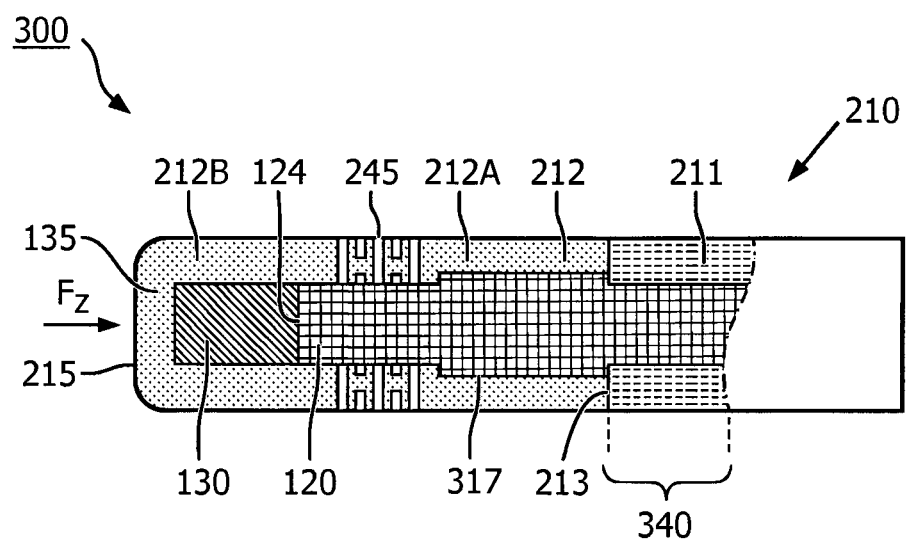
FIG. 3 is a simplified schematic diagram of a cut-away view of an optical shape sensing device including a force sensing region, according to a representative embodiment.

FIG. 3 is a simplified schematic diagram of a cut-away view of an optical shape sensing device including a force sensing region, according to a representative embodiment. Referring to FIG. 3, optical shape sensing device 300 is substantially the same as the optical shape sensing device 200, except that a force sensing region 340 is located in a portion of the flexible tubing 211 immediately adjacent to a proximal end of the rigid tube 212, next to the proximal rigid section 212A, as opposed to coinciding with the elastic segment 245.

That is, the optical shape sensing device 300 includes the elongated outer body 210, which includes the flexible tubing 211 and the rigid tube 212 attached to the flexible tubing 211. The optical shape sensing device 200 also includes the multicore optical fiber 120 extending through the elongated outer body 210, and a termination piece 130 attached to a distal tip 124 of the multicore optical fiber 120, as discussed above, and positioned within the rigid tube 212. As in the previous embodiment, shape sensing is enabled by the optical shape sensing device 300 along the multicore optical fiber 120 to the distal tip 135 of the termination piece 130.

The optical shape sensing device 300 further includes the elastic segment 245 located in the rigid tube 212 proximally from the termination piece 130. Adhesive 317 binds the multicore optical fiber 120 to the inner surface of the proximal rigid section 212A of the rigid tube 212, but not to the distal rigid section 212B. Accordingly, the multicore optical fiber 120 and the termination piece 130 are free to float within the distal rigid segment 212B and the elastic segment 245. Any compression (and axial strain) of the multicore optical fiber 120 responsive to an axial force $F_z$ exerted on the distal end 215 of the elongated body 210 would therefore occur just proximally to the proximal rigid section 212A of the rigid tube 212, which is fixed to the multicore optical fiber 120 by the adhesive 317. This compression (and axial strain) would be sensed through the force sensing region 340. Determination of the amount of axial force exerted on the distal end 215 involves measuring changes in the axial strain on the central optical fiber of the multicore optical fiber 120 at the force sensing region 340, as discussed above. The adhesive 317 may be an epoxy or an anaerobic adhesive material, for example, although different materials may be incorporated without departing from the scope of the present teachings.

In some applications, the rigidity of the rigid tube 212 at the distal end 215 of the elongated outer body 210 in FIGS. 2 and 3, for example, may limit the ability to maneuver the optical shape sensing device 200 or 300 in small lumens. Therefore, the force sensing region may be moved more proximally along the length of the multicore optical fiber 120. However, in order to determine axial forces at the distal end 215 of the elongated outer body 210, the axial forces must be transmitted along the flexible tubing 211 to the rigid tube 212.

Figure 4:
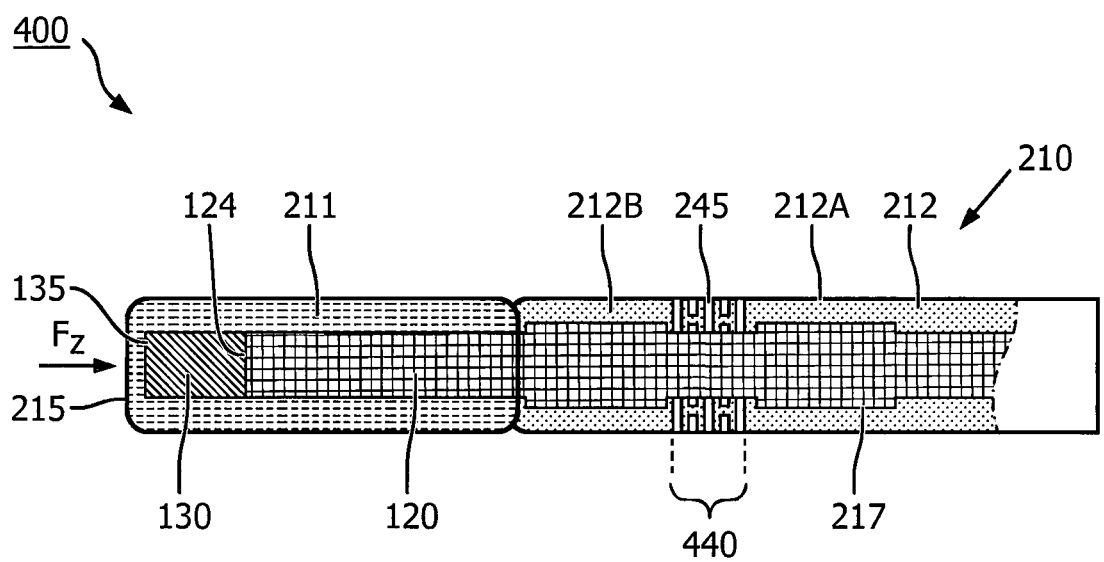
FIG. 4 is a simplified schematic diagram of a cut-away view of an optical shape sensing device including a more proximally located force sensing region, according to a representative embodiment.

FIG. 4 is a simplified schematic diagram of a cut-away view of an optical shape sensing device including a more proximally located force sensing region, according to a representative embodiment. Referring to FIG. 4, optical shape sensing device 400 is substantially the same as the optical shape sensing device 200, except that the relative locations of the flexible tubing 211 and the rigid tube 212 are reversed, with additional flexible tubing (not shown) on the proximal end of the rigid tube 212, enabling the flexibility for navigation through passages. The elastic segment 245 is located between the proximal rigid section 212A and the distal rigid section 212B of the rigid tube 212, and a force sensing region 440 of the optical shape sensing device 400 coincides with the elastic segment 245.

That is, the optical shape sensing device 400 includes the elongated outer body 210', which includes the flexible tubing 211 and the rigid tube 212 attached to the flexible tubing 211 at a proximal end 216 of the flexible tubing 211 (as opposed to being attached to the distal end 213). The optical shape sensing device 400 also includes the multicore optical fiber 120 extending through the elongated outer body 210', and a termination piece 130 attached to a distal tip 124 of the multicore optical fiber 120, as discussed above. The termination piece 130 is positioned within the flexible tubing 211. Shape sensing is enabled by the optical shape sensing device 400 along the multicore optical fiber 120 to the distal tip 135 of the termination piece 130.

The optical shape sensing device 400 further includes the elastic segment 245 located in the rigid tube 212 proximally from the termination piece 130 and the flexible tubing 211. Adhesive 217 binds the multicore optical fiber 120 to an inner surface of both the proximal rigid section 212A of the rigid tube 212, and the distal rigid section 212B of the rigid tube 212. The elastic segment 245 enables axial compression and expansion of the rigid tube 212 of the elongated outer body 210' responsive to an axial force $F_z$ exerted on the distal end 215 of the elongated body 210. No adhesive binds the termination piece 130 to the flexible tubing 211. Accordingly, the multicore optical fiber 120 and the termination piece 130 are free to float within the flexible tubing 211 and the elastic segment 245. Any compression (and axial strain) of the multicore optical fiber 120 responsive to an axial force $F_z$ exerted on the distal end 215 of the elongated outer body 210 would therefore occur in the elastic segment 245. Determination of the amount of axial force exerted on the distal end 215 involves measuring changes in the axial strain on the central optical fiber of the multicore optical fiber 120 at the force sensing region 340, as discussed above.

Figure 5:
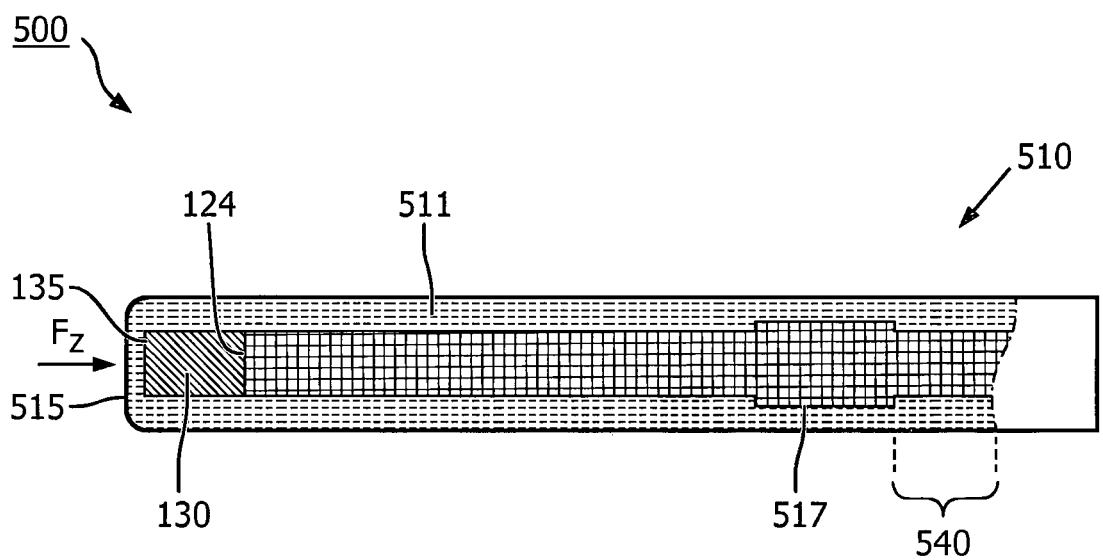
FIG. 5 is a simplified schematic diagram of a cut-away view of an optical shape sensing device including a force sensing region, with no rigid tube, according to a representative embodiment.

FIG. 5 is a simplified schematic diagram of a cut-away view of an optical shape sensing device including a force sensing region, according to a representative embodiment. Referring to FIG. 5, optical shape sensing device 500 does not include a rigid tube, such rigid tube 212. The multicore optical fiber 120 therefore extends entirely through flexible tubing (flexible tubing 511). A force sensing region 540 of the optical shape sensing device 500 is located proximally to a section of adhesive 517 between the multicore optical fiber 120 and the inner surface of the flexible tubing 511.

More particularly, the optical shape sensing device 500 includes an elongated outer body 510, which includes the flexible tubing 511. The multicore optical fiber 120 extends through the flexible tubing 511, and a termination piece 130 is attached to a distal tip 124 of the multicore optical fiber 120, as discussed above. The termination piece 130 is also located within the flexible tubing 511. Shape sensing is enabled by the optical shape sensing device 500 along the multicore optical fiber 120 to the distal tip 135 of the termination piece 130.

Adhesive 517 binds the multicore optical fiber 120 to the inner surface of the flexible tubing 511 proximally from the termination piece 130. In the depicted embodiment, the adhesive 517 is not immediately adjacent to the termination piece 130, but rather is located a distance from the termination piece 130, which is sufficient to allow some floating of the multicore optical fiber 120 before the location of the adhesive 517. In other words, the multicore optical fiber 120 and the termination piece 130 are free to float within the flexible tubing 511 prior to the adhesive 517, and the multicore optical fiber 120 is free to float within the flexible tubing 511 after the adhesive 517, as well. Any compression (and axial strain) of the multicore optical fiber 120 responsive to an axial force $F_z$ exerted on the distal end 515 of the elongated outer body 510 would therefore occur just proximally to the proximal to the location at which the multicore optical fiber 120 is fixed to the inner surface of the flexible tubing 511 by the adhesive 517. This compression (and axial strain) would be sensed through the force sensing region 540. Determination of the amount of axial force exerted on the distal end 515 involves measuring changes in the axial strain on the central optical fiber of the multicore optical fiber 120 at the force sensing region 540, as discussed above. The adhesive 517 may be an epoxy or an anaerobic adhesive material, for example, although different materials may be incorporated without departing from the scope of the present teachings.

FIG. 5 shows a similar concept as FIG. 4, but without the rigid tube 212. The multicore optical fiber 120 is fixed directly to the flexible tubing 511 in one location by the adhesive 517, and then any compression in the flexible tubing 511 will be transmitted to the fixed segment. Hence, the force sensing region 540 would occur proximally to the fixed section. Applying the adhesive 517 in a middle portion, for example, of a long elongated outer body 510 may be challenging, though. The fixed section defined by the adhesive 517 should be very small in comparison to the length of the elongated outer body 510, and placing the adhesive 517 involves the multicore optical fiber 120 being pushed through several centimeters of the flexible tubing 511. Alternative materials to the adhesive 517 may be, such as UV curable or heat curable glue, which would allow a smaller diameter elongated outer body 510 to be used. Accordingly, the multicore optical fiber 120 may be fixed to the flexible tubing 511 after it has been pushed through the flexible tubing 511. In other words, use of UV curable or heat curable glue, for example, enables external determination of the location(s) at which the multicore optical fiber 120 is fixed to the flexible tubing 511, even if the glue is located (but not cured) outside that location(s).

Figure 6:
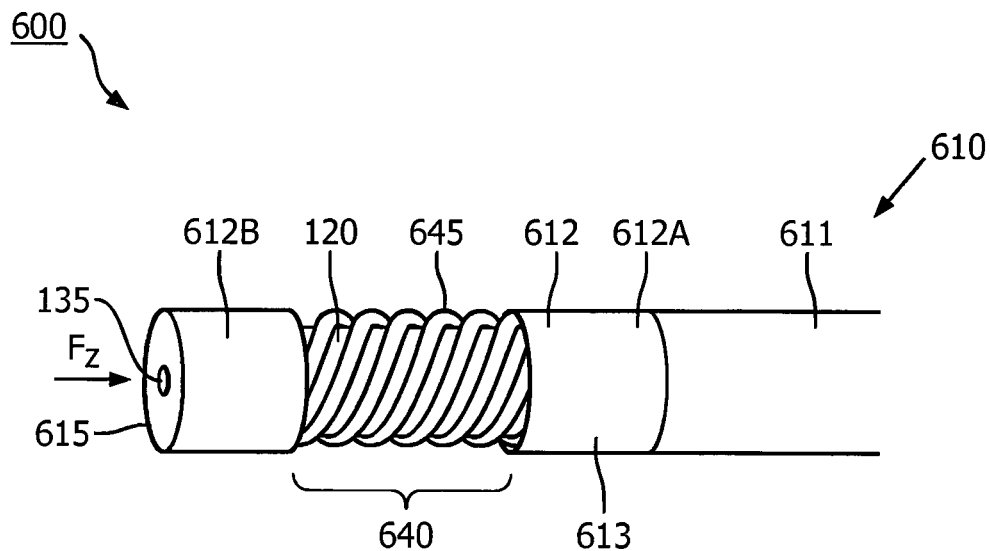
FIG. 6 is a plan view of an optical shape sensing device including a force sensing region having a coil spring, according to a representative embodiment.

FIG. 6 is a plan view of an optical shape sensing device including a force sensing region having a coil spring, according to a representative embodiment.

Referring to FIG. 6, optical shape sensing device 600 includes an elongated outer body 610, which includes flexible tubing 611 and rigid tube 612 attached to the flexible tubing 611. In the depicted embodiment, the rigid tube 612 is attached to a distal end 613 of the flexible tubing 611. The flexible tubing 611 enables the maneuvering of the optical shape sensing device 600 through a passage, as discussed above. The optical shape sensing device 600 also includes multicore optical fiber 120 extending longitudinally through the elongated outer body 610, and a termination piece (e.g., termination piece 130, not shown in FIG. 6) attached to a distal tip of the multicore optical fiber 120, as discussed above. The termination piece is positioned within the rigid tube 612, and includes the distal tip 135, which may substantially coincide with a distal end 615 of the elongated outer body 610. Shape sensing is enabled by the optical shape sensing device 600 along the multicore optical fiber 120 clear to the distal tip 135 of the termination piece.

The optical shape sensing device 600 further includes a force sensing region 640 integrated with the rigid tube 612 of the elongated outer body 610. The rigid tube 612 has a proximal rigid section 612A, a distal rigid section 612B, and a multithread coil spring 645 located in between, where the multicore optical fiber runs through the coil spring 645. In the depicted embodiment, the force sensing region 640 of the optical shape sensing device 600 coincides with the coil spring segment 645, which is the elastic segment of the elongated outer body 610. That is, the coil spring 645 enables axial compression and expansion of the rigid tube 612 responsive to an axial force $F_z$ exerted on the distal end 615 of the elongated body 610. Use of the coil spring 645 enables the elastic segment to be longer than other types of elastic segments, such as a pattern of slits (e.g., elastic segment 245) or a laser cut design.

The force sensing region 640, together with the processing unit 150 (not shown in FIG. 6), is configured to sense the amount of axial force $F_z$ exerted on the distal end 615 of the elongated outer body 610, which corresponds to the distal end of the rigid tube 612. When the coil spring 645 compresses, the optical fiber 120 between the proximal and distal rigid sections 612A and 612B also compresses, and the axial strain in this area is used to calculate the applied force. The optical fiber 120 may be fixed to the proximal and distal rigid sections 612A and 612B using adhesive (not shown in FIG. 6), similar to the adhesive 217 discussed above. Determination of the amount of axial force exerted on the distal end 615 involves measuring changes in axial strain on the central optical fiber of the multicore optical fiber 120 at the force sensing region 640, as discussed above.

Figure 7:
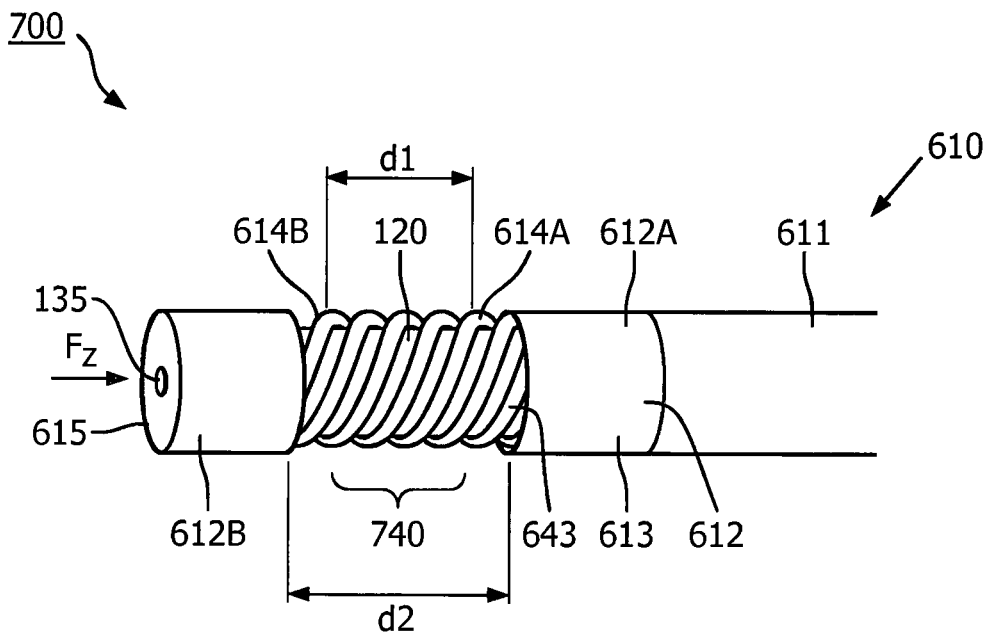
FIG. 7 is a plan view of an optical shape sensing device including a force sensing region having a coil spring, according to a representative embodiment.

FIG. 7 is a simplified schematic diagram of a cut-away view of an optical shape sensing device including a force sensing region having a coil spring, according to a representative embodiment. Referring to FIG. 7, optical shape sensing device 700 is substantially the same as the optical shape sensing device 600, with the addition of proximal and distal rigid extensions 614A and 614B that extend within the coil spring 645 from the proximal and distal rigid sections 612A and 612B. Extending these solid parts (proximal and distal rigid extensions 614A and 614B) inside the coil spring 645 results in the axial strain induced in the multicore optical fiber 120 by the axial force $F_z$ being larger than the axial strain induced in the coil spring 645.

More particularly, application of an axial force $F_z$ results in a compression of the rigid tube 612 assembly indicated by δd. The axial strain over the length (d2) of the coil spring 645 is ε2=δd/d2, whereas the axial strain over the length (d1) of the exposed portion of the multicore optical fiber 120 (i.e., the space within the coil spring 645 between proximal and distal rigid extensions 614A and 614B) is ε1=δd/d1. Since d2>d1, it follows that ε1>ε2, which will result effectively in increased force sensitivity in the force sensing region 740 of the optical shape sensing device 700, e.g., as compared to the force sensing region 640 of the optical shape sensing device 600.

Figure 8A:
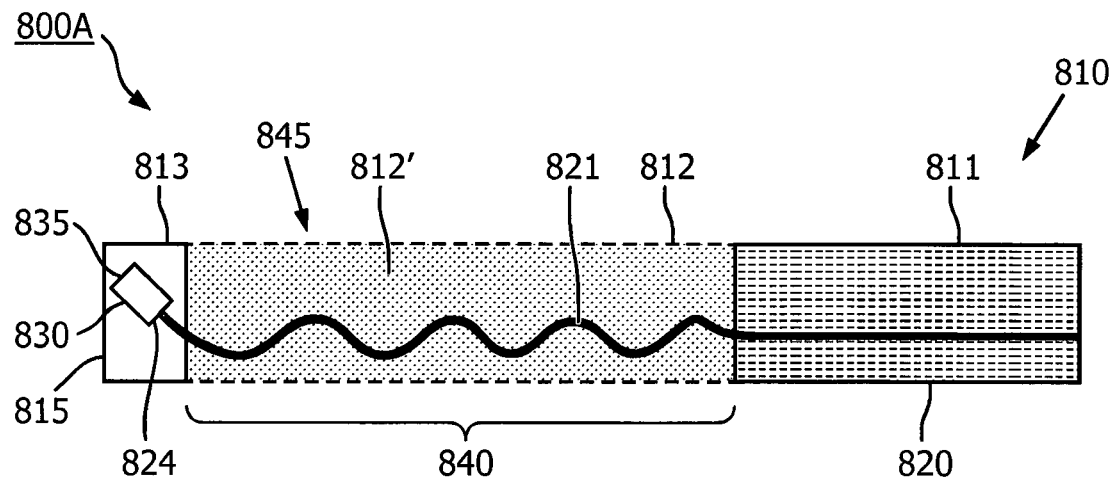
FIG. 8A is a simplified cross-sectional diagram of an optical shape sensing device including a force sensing region in which multicore optical fiber has helical pattern, according to a representative embodiment.

FIG. 8A is a simplified cross-sectional diagram of an optical shape sensing device including a force sensing region in which optical fiber has helical pattern, according to a representative embodiment.

Referring to FIG. 8A, optical shape sensing device 800A includes an elongated outer body 810, which includes proximal flexible tubing 811, distal flexible tubing 812 attached to the proximal flexible tubing 811, and distal tube 813 attached to the distal flexible tubing 812. The proximal and distal flexible tubing 811 and 812 enable the maneuvering of the optical shape sensing device 800A through a passage, as discussed above. The optical shape sensing device 800A also includes multicore optical fiber 820 extending longitudinally through the elongated outer body 810, and a termination piece 830 attached to a distal tip 824 of the multicore optical fiber 820, as discussed above. The termination piece 830 is located within the distal tube 813 and includes a distal tip 835, which may substantially coincide with a distal end 815 of the elongated outer body 810. Shape sensing is enabled by the optical shape sensing device 800 along the multicore optical fiber 820 to the distal tip 835 of the termination piece 830. The composition of the multicore optical fiber 820 is substantially the same as the multicore optical fiber 120, discussed above.

In the depicted embodiment, the multicore optical fiber 820 includes a helical portion 821 having a helical pattern. The helical portion 821 is embedded in compliant material 812' within the distal flexible tubing 812, which increases axial sensitivity in multiple directions over other embodiments in which the multicore optical fiber has no helical patter. The helical portion 821 defines a deformation region 845, and the force sensing region 840 of the optical shape sensing device 800 coincides with the deformation region 845. The compliant material 812' may be silicon (Si), for example, although other materials with similar compliant properties may be incorporated without departing from the scope of the present teachings. Incorporation of the helical portion 821 engages multiple modes of deformation to provide higher resolution force-from-strain sensing.

The deformation region 845 enables axial compression and expansion of the distal flexible tubing 812 (and the compliant material 812' therein) of the elongated outer body 810 responsive to an axial force $F_z$ exerted on the distal end 815 of the elongated body 810. The force sensing region 840, together with the processing unit 150 (not shown in FIG. 8), is configured to sense the amount of axial force exerted on the distal end 815 of the elongated outer body 810. When the deformation region 845 compresses, the helical portion 821 of the multicore optical fiber 820 deforms in a manner reflected by the compliant material 812', and thus captured by the force sensing region 840. Due to freedom of movement of the helical portion 821 within the compliant material 812', forces in directions other than an axial direction may be detected via the force sensing region 840.

Figure 8B:
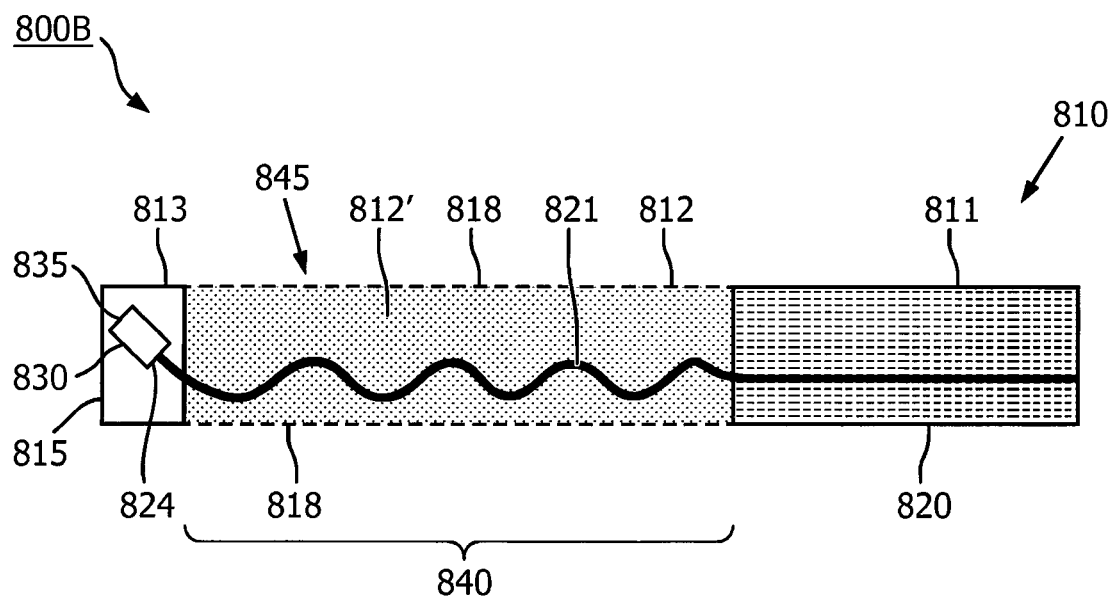
FIG. 8B is a simplified cross-sectional diagram of an optical shape sensing device including a force sensing region in which multicore optical fiber has helical pattern, according to a representative embodiment.

FIG. 8B is a simplified cross-sectional diagram of an optical shape sensing device including a force sensing region in which optical fiber has helical pattern, according to a representative embodiment. Referring to FIG. 8B, optical shape sensing device 800B is substantially the same as the optical shape sensing device 800A, with the addition of stiffening members 818, formed along the distal flexible tubing 812 to increase lateral stiffness. The stiffening members 818 may be formed of any lightweight, substantially rigid material, such as titanium, polyether ether ketone, polypropylene, nylon, polyimide, acetal, or acrylonitrile butadiene styrene, for example. Also, the stiffening members 818 may be arranged on an outer surface of the distal flexible tubing 812, as shown, or between the distal flexible tubing 812 and the compliant material 812', although other arrangements of the distal flexible tubing 812 may be incorporated without departing from the scope of the present teachings.

Figure 9:
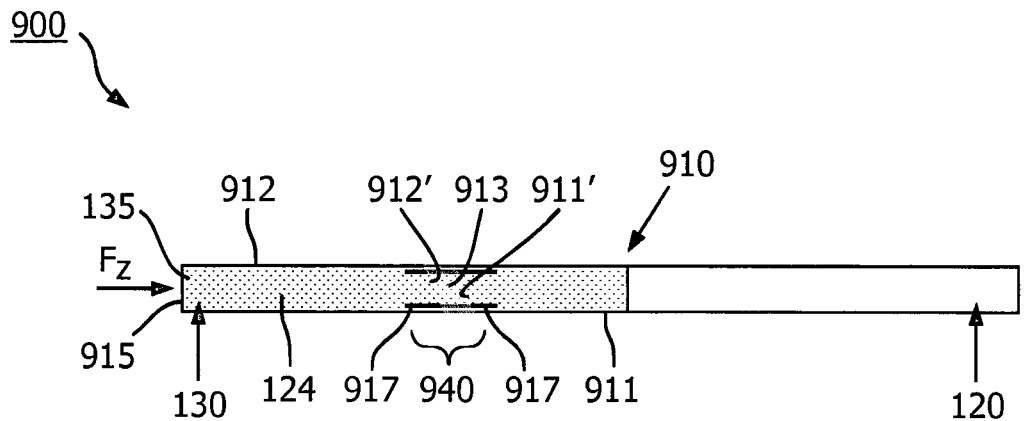
FIG. 9 is a simplified cross-sectional diagram of an optical shape sensing device including a force sensing region for sensing torsion, according to a representative embodiment.

FIG. 9 is a simplified cross-sectional diagram of an optical shape sensing device including a force sensing region for sensing torsion, according to a representative embodiment.

Referring to FIG. 9, optical shape sensing device 900 includes an elongated outer body 910 configured to maneuver through a passage, as discussed above. The elongated outer body 910 includes a proximal (first) substantially rigid portion 911 and a distal (second) substantially rigid portion 912, separated by a space 913 between the proximal and distal substantially rigid portions 911 and 912. The proximal and distal substantially rigid portions 911 and 912 may be formed of the same material(s) as the rigid tube 212, for example, discussed above with reference to FIG. 2.

The optical shape sensing device 900 also includes multicore optical fiber 120 extending longitudinally through the elongated outer body 910, and a termination piece 130 attached to the distal tip 124 of the multicore optical fiber 120, as discussed above. The termination piece 130 is positioned within the distal substantially rigid portion 92, and includes the distal tip 135, which may substantially coincide with a distal end 915 of the elongated outer body 910. Shape sensing is enabled by the optical shape sensing device 900 along the multicore optical fiber 120 to the distal tip 135 of the termination piece 130.

Adhesive 917 binds the multicore optical fiber 120 to portions of the inner surfaces of the proximal substantially rigid portion 911 and the distal substantially rigid portion 912, respectively, adjacent the space 913. The adhesive 917 prevents the multicore optical fiber 120 from sliding within the proximal and distal substantially rigid portions 911 and 912. The adhesive 917 may be an epoxy or an anaerobic adhesive material, for example, although different materials may be incorporated without departing from the scope of the present teachings.

In the depicted embodiment, the proximal substantially rigid portion 911 has a first angled edge 911' and the distal substantially rigid portion 912 has a second angled edge 912' complementary to the first angled edge 911'. The first and second angled edges 911' and 912' face one another across the space 913, and are shaped so that, when the elongated outer body 910 is compressed, the first and second angled edges 911' and 912' rotate with respect to one another, causing the multicore optical fiber 120 (adhered to the inner surfaces of the proximal and distal substantially rigid portions 911 and 912) to twist within the space 913. A force sensing region 940, which substantially coincides with the space 913, is configured to sense the amount of twisting (torsion) of the multicore optical fiber 120 in response to the axial force $F_z$ exerted on the distal end 915 of the elongated body 910. Generally, the twisting of the multicore optical fiber 120 causes the at least two additional optical fibers, helically wrapped around the central optical fiber of the multicore optical fiber 120, to unravel or tighten to an extent proportional to the amount of axial force being exerted on the distal end 915. Thus, in an embodiment, the extent of unraveling or tightening may be used to determine the axial force $F_z$.

The force sensing region 940, together with the processing unit 150 (not shown in FIG. 9), is configured to sense the amount of axial force exerted on the distal end 915 of the elongated outer body 910, which corresponds to the distal end of the distal substantially rigid portion 912. When the proximal and distal substantially rigid portions 911 and 912 rotate with respect to one another, the multicore optical fiber 120 twists, the amount of twisting is used by the processing unit 150 to calculate the applied axial force, in accordance with a predetermined algorithm. Determination of torsion is described, for example, in U.S. Pat. No. 8,773,650 to Froggatt et al. (Jul. 8, 2014), and in U.S. Pat. No. 7,772,541 to Froggatt et al. (Aug. 10, 2010), both of which are hereby incorporated by reference in their entireties.

Figure 10:
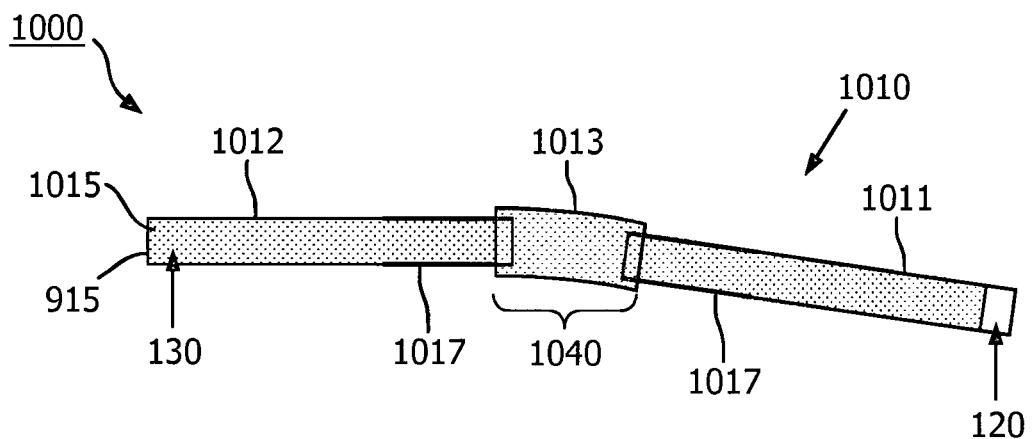
FIG. 10 is a simplified cross-sectional diagram of an optical shape sensing device including a force sensing region for sensing buckling of the optical shape sensing device, according to a representative embodiment.

FIG. 10 is a simplified cross-sectional diagram of an optical shape sensing device including a force sensing region for sensing buckling of the optical shape sensing device, according to a representative embodiment.

Referring to FIG. 10, optical shape sensing device 1000 includes an elongated outer body 1010 configured to maneuver through a passage, as discussed above. The elongated outer body 1010 includes a proximal (first) substantially rigid portion 1011 and a distal (second) substantially rigid portion 1012, and flexible tubing 1013 connected between the proximal and distal substantially rigid portions 1011 and 1012. The flexible tubing 1013 enables the proximal and distal substantially rigid portions 1011 and 1012 to move relative to one another, enabling bending or buckling of the elongated outer body 1010. The proximal and distal substantially rigid portions 1011 and 1012 may be formed of the same material(s) as the rigid tube 212, for example, and the flexible tubing 1013 may by formed of the same material(s) as the flexible tubing 211, for example, discussed above with reference to FIG. 2.

The optical shape sensing device 1000 also includes multicore optical fiber 120 extending longitudinally through the elongated outer body 1010, and a termination piece 130 attached to the distal tip 124 of the multicore optical fiber 120, as discussed above. The termination piece 130 is positioned within the distal substantially rigid portion 1012, and includes the distal tip 135, which may substantially coincide with a distal end 1015 of the elongated outer body 1010. Shape sensing is enabled by the optical shape sensing device 1000 along the multicore optical fiber 120 to the distal tip 135 of the termination piece 130.

The optical shape sensing device 1000 further includes a force sensing region 1040 integrated with the elongated outer body 1010. More particularly, the force sensing region 1040 substantially coincides with a bendable portion of the flexible tubing 1013 (e.g., where there is no overlap between the flexible tubing 1013 and either of the proximal substantially rigid portion 1011 or the distal substantially rigid portion 1012). The force sensing region 1040 is configured to sense an axial force exerted $F_z$ on the distal end 1015 of the elongated body 1010 based on determining an amount of buckling experienced by the flexible tubing 1013 and sensed by the force sensing region 1040 in response to the axial force $F_z$. That is, the force sensing region 1040 senses the axial force $F_z$ via changes in curvature of the multicore optical fiber 120, or strain on the multicore optical fiber 120, within the flexible tubing 1013 resulting from buckling.

Adhesive 1017 binds the multicore optical fiber 120 to portions of the inner surfaces of the proximal substantially rigid portion 1011 and the distal substantially rigid portion 1012, respectively, adjacent the flexible tubing 1013. The adhesive 1017 prevents the multicore optical fiber 120 from sliding within the proximal and distal substantially rigid portions 1011 and 1012 to enable a more accurate determination of buckling caused by application of the axial force $F_z$. The adhesive 1017 may be an epoxy or an anaerobic adhesive material, for example, although different materials may be incorporated without departing from the scope of the present teachings.

The force sensing region 1040, together with the processing unit 150 (not shown in FIG. 10), is configured to sense the amount of axial force exerted on the distal end 1015 of the elongated outer body 210, which corresponds to the distal end of the distal substantially rigid portion 1012. When the flexible tubing 1013 buckles, the bare multicore optical fiber 120 also buckles, and the amount (or degree) of buckling is used by the processing unit 150 to calculate the applied axial force, in accordance with a predetermined algorithm. Buckling may be sensed, for example, through a change in the curvature of the multicore optical fiber. The greater the amount of buckling, the greater the curvature change. A calibration procedure may be used to model force as a function of curvature. Determination of curvature and changes thereto is described, for example, in U.S. Pat. No. 8,773,650 to Froggatt et al. (Jul. 8, 2014), and in U.S. Pat. No. 7,772,541 to Froggatt et al. (Aug. 10, 2010), both of which are hereby incorporated by reference in their entireties.

In other embodiments, the design of the outer surface of a conventional optical shape sensing device (e.g., a guidewire or catheter shaft) may be modified. For example, conventional guidewires and catheters may be made of nitinol, which is "braided," and then coated with different types of materials (e.g., soft and flexible or more rigid). That is, the entire outer surface or outer body of the optical sensing device may be braided in the same (conventional) manner, but the material covering the braided design may differ in flexibility in various sections, depending on anticipated functionality, respectively. Alternatively, or in addition, construction the braided design may differ in various sections to change flexibility. That is, the conventional braided design may still be used in the majority of the optical sensing device, while a relatively small section the nitinol may be formed into a spring-like design that compresses in response to applied axial forces.

Figure 11A:
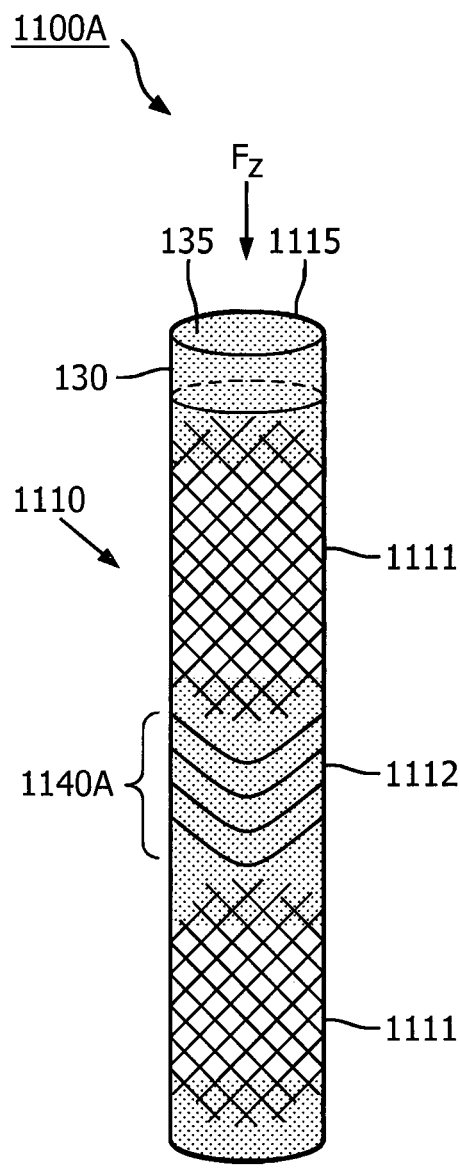
FIG. 11A is a simplified transparent plan view of an optical shape sensing device including a force sensing region, according to a representative embodiment.

FIG. 11A is a simplified transparent plan view of an optical shape sensing device including a force sensing region, according to a representative embodiment.

Referring to FIG. 11A, optical shape sensing device 1100A includes an elongated outer body 1110, which includes braided design portions 1111 and a spring design portion 1112 formed integrally with and between the braided design portions 1111. The spring design portion 1112 compresses in response to applied axial forces, such as axial force $F_z$.

A multicore optical fiber (not shown) runs longitudinally through the elongated outer body 1110, and is fixed to the braided design portions 1111, e.g., using adhesive, on either end of the spring design portion 1112. A termination piece 130 is attached to a distal tip of the multicore optical fiber, and includes a distal tip 135, which may substantially coincide with a distal end 1115 of the elongated outer body 1110. A force sensing region 1140A of the optical shape sensing device 1100 substantially coincides with the spring design portion 1112. The force sensing region 1140, together with the processing unit 150 (not shown in FIG. 11A), is configured to determine the amount of axial force exerted on a distal end 1115 of the elongated outer body 1110 by sensing compression of the spring design portion 1112 responsive to the axial force $F_z$.

Figure 11B:
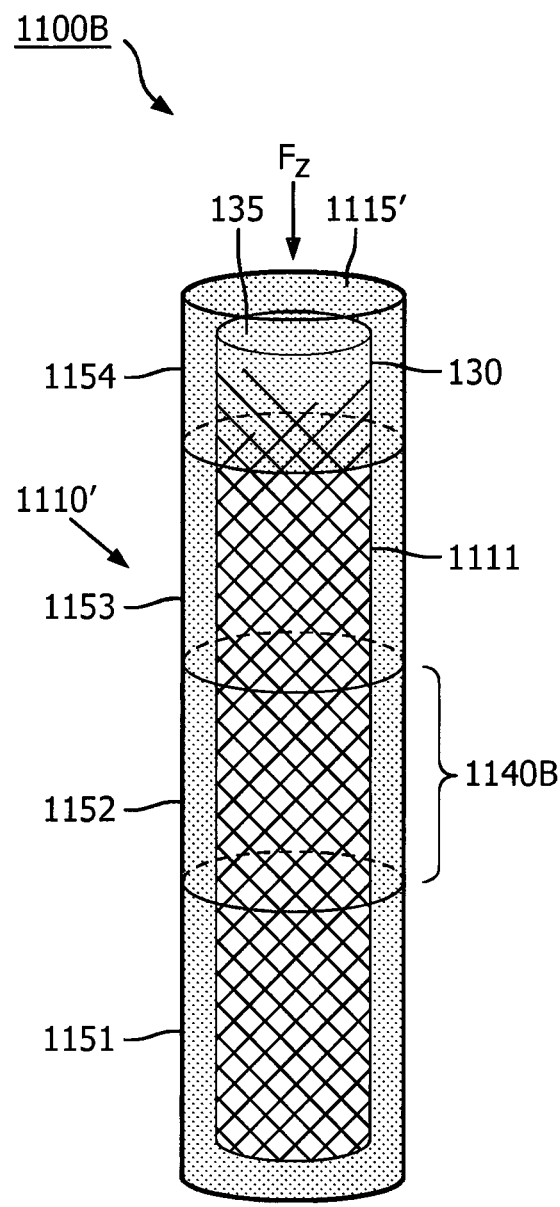
FIG. 11B is a simplified transparent plan view of an optical shape sensing device including a force sensing region, according to a representative embodiment.

FIG. 11B is a simplified transparent plan view of an optical shape sensing device including a force sensing region, according to a representative embodiment.

Referring to FIG. 11B, optical shape sensing device 1100B includes an elongated outer body 1110', which includes a braided design portion 1111 along substantially the entire length (i.e., there is not spring design portion). Rather, an elastic segment of the elongated outer body 1110' is provided by use of different materials covering the braided design portion 1111. In the depicted embodiment, the elongated outer body 1110' is covered by a first material in first material segment 1151, a second material in second material segment 1152, a third material in third material segment 1153, and a fourth material in fourth material segment 1154. The first and third materials, which may be the same, are rigid or substantially rigid materials, and the third material is a standard material for covering a termination piece (e.g., termination piece 130), such as standard PTFE, for example. The second material covering the second material segment 1152 is an elastic material, such as silicone or any biocompatible rubber-like material, for example. Accordingly, the second material segment 1152 compresses in response to applied axial forces, such as axial force $F_z$.

A multicore optical fiber (not shown) runs longitudinally through the elongated outer body 1110', and is fixed to at least the first and third material segments 1151 and 1153, e.g., using adhesive, on either side of the end of the second material segment 1152. A termination piece 130 is attached to a distal tip of the multicore optical fiber, and includes a distal tip 135, which may substantially coincide with a distal end 1115' of the elongated outer body 1110'. A force sensing region 1140B of the optical shape sensing device 1100B substantially coincides with the second material segment 1152. The force sensing region 1140B, together with the processing unit 150 (not shown in FIG. 11B), is configured to determine the amount of axial force exerted on a distal end 1115' of the elongated outer body 1110' by sensing compression of the second material segment 1152 responsive to the axial force $F_z$.

Figure 12:
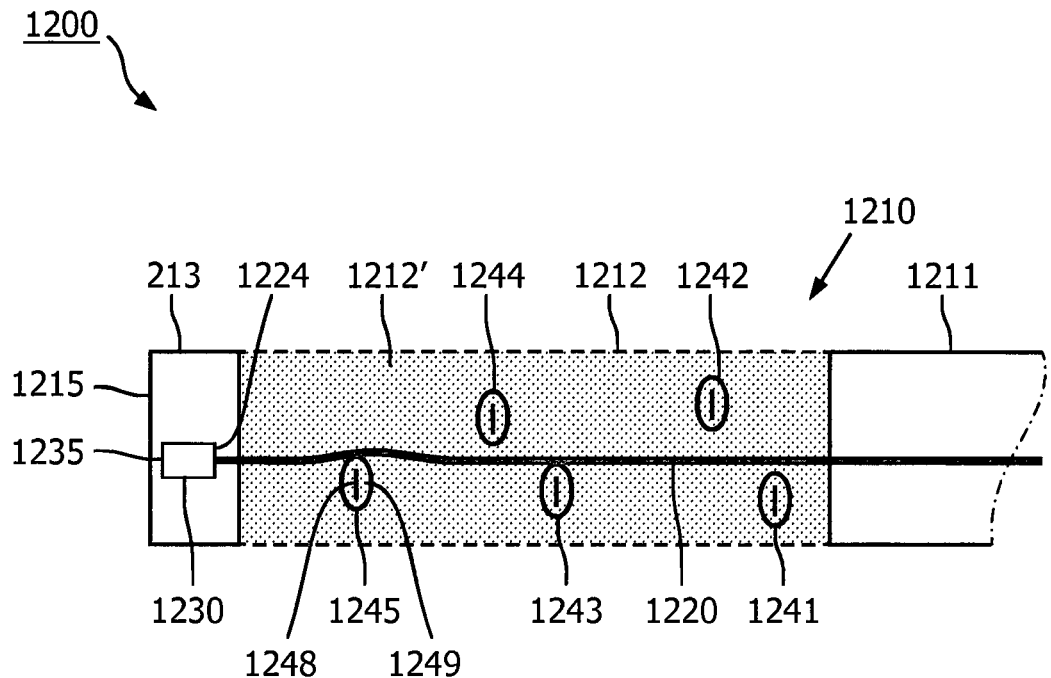
FIG. 12 is a simplified cross-sectional diagram of an optical shape sensing device including multiple force sensing regions embedded in compliant material, according to a representative embodiment.

FIG. 12 is a simplified cross-sectional diagram of an optical shape sensing device including multiple force sensing regions embedded in compliant material, according to a representative embodiment.

Referring to FIG. 12, optical shape sensing device 1200 includes an elongated outer body 1210, which includes proximal flexible tubing 1211, distal flexible tubing 1212 attached to the proximal flexible tubing 1211, and distal tube 1213 attached to the distal flexible tubing 1212. The proximal and distal flexible tubing 1211 and 1212 enable the maneuvering of the optical shape sensing device 1200 through a passage, as discussed above. The optical shape sensing device 1200 also includes multicore optical fiber 1220 extending longitudinally through the elongated outer body 1210, and a termination piece 1230 attached to a distal tip 1224 of the multicore optical fiber 1220, as discussed above. In the depicted embodiment, a portion of the multicore optical fiber 1220 is embedded in compliant material 1212' within the distal flexible tubing 1212. The termination piece 1230 is located within the distal tube 1213, and includes a distal tip 1235, which may substantially coincide with a distal end 1215 of the elongated outer body 1210. Shape sensing is enabled by the optical shape sensing device 1200 along the multicore optical fiber 1220 to the distal tip 1235 of the termination piece 1230. The composition of the multicore optical fiber 1220 is substantially the same as the multicore optical fiber 120, discussed above.

The optical shape sensing device 1200 further includes multiple force sensing regions 1241, 1242, 1243, 1244 and 1245 embedded in the compliant material 1212', surrounding the multicore optical fiber 1220. Each of the force sensing regions 1241 to 1245 includes a solid element 1248 inside a corresponding perforation 1249 through the distal flexible tubing 1212 and the compliant material 1212'. The solid element 1248 may be a metal bead, for example, and the compliant material 1212' may be silicon (Si), for example, although other compliant materials with similar properties, respectively, may be incorporated, without departing from the scope of the present teachings.

The force of a contact on the termination piece 1230 and/or the distal flexible tubing 1212 (axial or lateral) pushes one or more of the solid elements 1248 inside the distal flexible tubing 1212. This changes the position of the one or more solid elements 1248, and thus the shape of the compliant material 1212', creating a small change in the shape of the optical shape sensing device 1200 corresponding to the contact point. In the example depicted in FIG. 12, a substantial lateral force (not shown) has displaced at least the solid element 1248 of the force sensing region 1245, such that it is in contact with the multicore optical fiber 1220 (changing the shape of the multicore optical fiber 1220, as well as the shape of the compliant material 1212'). The extent of the displacement is sensed by at least the force sensing region 1245 (and possibly one or more of the other force sensing regions 1241-1244). Therefore, the force sensing regions 124-1245, together with the processing unit 150 (not shown in FIG. 12), are configured to sense the amount of lateral forces, as well as axial force, exerted on the termination piece 1230 and/or the distal flexible tubing 1212.

Figure 13:
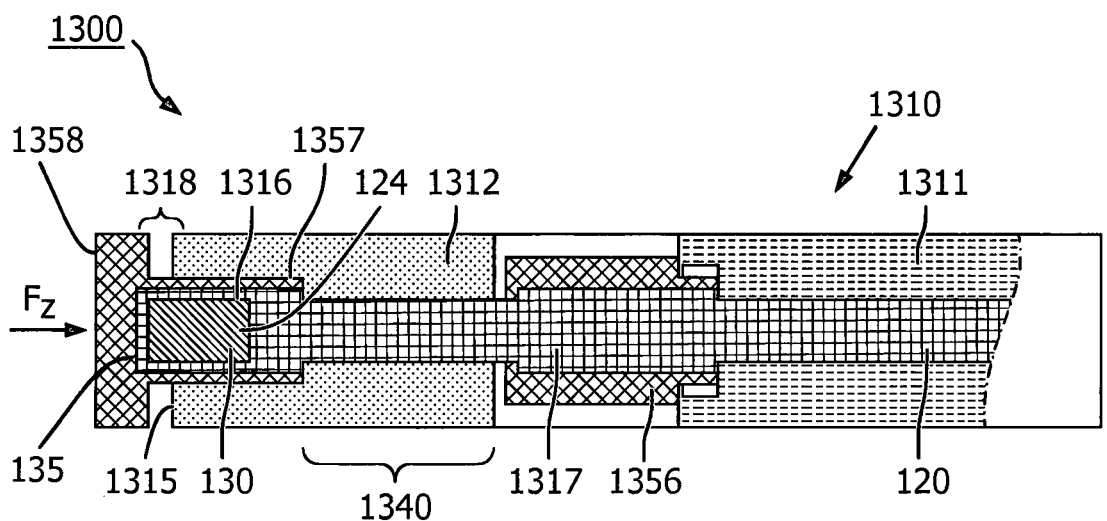
FIG. 13 is a simplified schematic diagram of a cut-away view of an optical shape sensing device including a force sensing region and a stopper, according to a representative embodiment.

FIG. 13 is a simplified schematic diagram of a cut-away view of an optical shape sensing device including a force sensing region and a stopper, according to a representative embodiment.

Referring to FIG. 13, optical shape sensing device 1300 includes an elongated outer body 1310, which includes flexible tubing 1311 and substantially rigid tube 1312 attached to the flexible tubing 1311. In the depicted embodiment, the rigid tube 1312 is attached to a distal end of the flexible tubing 1311, and may have varying degrees of rigidity, although the rigid tube 1312 is less flexible than the flexible tubing 1311. The flexible tubing 1311 enables the maneuvering of the optical shape sensing device 1300 through a passage, as discussed above. The optical shape sensing device 1300 further includes a disk 1358 attached to distal inner tubing 1357, which extends into a distal side of the rigid tube 1312 through a distal end 1315 of the elongated outer body 1310. In an uncompressed state, the disk 1358 is spaced apart from the distal end 1315 (which may also be referred to as a stopper) by gap 1318, as shown in FIG. 13.

The optical shape sensing device 1300 also includes multicore optical fiber 120 extending longitudinally through the elongated outer body 1310, and termination piece 130 attached to the distal tip 124 of the multicore optical fiber 120, as discussed above. The termination piece 130 is positioned within the rigid tube 1312, and has a distal tip 135. More particularly, the termination piece 130 and at least a portion of the multicore optical fiber 120 are positioned within the distal inner tubing 1357, which is inside the rigid tube 1312. The termination piece 130 and the at least a portion of the multicore optical fiber 120 are bound to the inside surface of the distal inner tubing 1357 using adhesive 1316. In the uncompressed stated, the distal tip 135 (inside the distal inner tubing 1357) extends beyond the distal end 1315 (stopper) of the elongated outer body 1310, as discussed below. Shape sensing is enabled by the optical shape sensing device 1300 along the multicore optical fiber 120 clear to the distal tip 135 of the termination piece 130.

A force sensing region 1340 is integrated with the elongated outer body 1310 in the rigid tube 1357. In an embodiment, the force sensing region 1340 is located between a proximal end of the distal inner tubing 1357 and a distal end of additional inner tubing 1356 located at a proximal side of the rigid tube 1312. A portion of the multicore optical fiber 120 extends through the additional inner tubing 1356, and is bound to an inner surface of the additional inner tubing 1356 by adhesive 1317. Thus, the force sensing region 1340 is effectively defined by an area between the proximal end of the distal inner tubing 1357 and the distal end of the additional inner tubing 1356. This focuses axial compression and expansion in the force sensing region 1340 within the defined area responsive to an axial force $F_z$ exerted on the disk 1358. The adhesive 1316 and 1317 may be an epoxy or an anaerobic adhesive material, for example, although different materials may be incorporated without departing from the scope of the present teachings.

Accordingly, when the axial force $F_z$ is exerted on the disk 1358, the rigid tube 1312 and the multicore optical fiber 120 compress within the force sensing region 120, and the gap 1318 becomes smaller (closes). Depending on the magnitude of the axial force $F_z$, the compression continues until the gap 1318 closes completely, that is, the disk 1358 is in physical contact with the distal end 1315. Thus, the size of the gap 1318 limits the amount of axial force (and the extent of compression of the force sensing region 1340) exerted on the termination piece 130 and the multicore optical fiber 120, thereby protecting the multicore optical fiber 120 from breakage in the force sensing region 1340 or elsewhere. The gap size may be selected based on mechanical properties of the multicore optical fiber 120 and the termination piece 130, as well as the maximum amount of force a user wants to detect.

In addition, the force sensing region 1340, together with the processing unit 150 (not shown in FIG. 13), are configured to sense the compression and determine the amount of axial force exerted on the disk 1358 and/or the distal end 1315 of the elongated outer body 1310. The axial strain in the area of the force sensing region 1340 is used to calculate the applied force. Determination of the amount of axial force exerted on the disk 1358 and/or the distal end 1315 involves measuring changes in axial strain on the central optical fiber of the multicore optical fiber 120, as discussed above.

While various embodiments have been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An optical shape sensing device comprising:
    an elongated outer body comprising flexible tubing configured to maneuver through a passage;
    a multicore optical fiber extending through the elongated outer body, and enabling shape sensing by tracking deformation of the multicore optical fiber along a length of the multicore optical fiber;
    a termination piece attached to a distal tip of the multicore optical fiber; and
    a force sensing region integrated with the elongated outer body and configured to enable determining of an axial force exerted on a distal end of the elongated outer body, where the multicore optical fiber is arranged in the force sensing region to optically sense changes in response to this axial force,
    wherein the shape sensing occurs along the multicore optical fiber to a distal tip of the termination piece.

2. The device of claim 1, wherein the elongated outer body further comprises a rigid tube attached to the flexible tubing.

3. The device of claim 2, wherein the rigid tube is attached to a distal end of the flexible tubing, the termination piece being positioned within the rigid tube.

4. The device of claim 3, wherein the rigid tube includes an elastic segment located proximally from the termination piece responsive to the axial force exerted on the distal end of the elongated body.

5. The device of claim 4, wherein adhesive binds the multicore optical fiber to the rigid tube at distal and proximal sides of the elastic segment, and
    wherein the force sensing region corresponds to the elastic segment.

6. The device of claim 5, wherein the elastic segment comprises a pattern of slits around an outer circumference of the rigid tube.

7. The device of claim 5, wherein the elastic segment comprises a coil spring between two rigid end portions of rigid tube.

8. The device of claim 3, wherein adhesive binds the multicore optical fiber to the rigid tube at only a proximal side of the elastic segment, and
    wherein the force sensing region is located in a portion of the flexible tubing immediately adjacent to a proximal end of the rigid tube.

9. The device of claim 8, wherein the elastic segment comprises a pattern of slits around an outer circumference of the rigid tube.

10. The device of claim 8, wherein the elastic segment comprises a coil spring between rigid end portions of rigid tube.

11. The device of claim 2, wherein the rigid tube is attached between distal and proximal portions of the flexible tubing, the termination piece being positioned within the distal portion of the flexible tubing,
    wherein the rigid tube includes an elastic segment, enabling axial compression and expansion of the elastic segment responsive to the axial force exerted on the distal end of the elongated body,
    wherein adhesive binds the multicore optical fiber to the rigid tube at distal and proximal sides of the elastic segment, and
    wherein the force sensing region corresponds to the elastic segment.

12. The device of claim 1, wherein the termination piece is positioned within the flexible tubing,
wherein adhesive binds the multicore optical fiber to a portion of the flexible tubing in an adhesive region located proximal to the termination piece, and
wherein the force sensing region is located in another portion of the flexible tubing immediately adjacent to a proximal end of the adhesive region.

13. The device of claim 1, further comprising:
compliant material between the multicore optical fiber and an inner surface of the elongated outer body in a deformation region of the multicore optical fiber, the multicore optical fiber having helical pattern within the deformation region, and
wherein the force sensing region corresponds to the deformation region.

14. The device of claim 13, further comprising:
stiffening rods in the compliant material located in the deformation region, the stiffening rods increasing lateral stiffness of the deformation region.

15. An optical shape sensing device comprising:
an elongated outer body configured to maneuver through a passage, the elongated outer body comprising a first substantially rigid portion, a second substantially rigid portion, and a flexible portion connected between the first and second substantially rigid portions;
a multicore optical fiber extending through the elongated outer body and enabling shape sensing by tracking positioning of the multicore optical fiber along a length of the multicore optical fiber;
a termination piece attached to a distal tip of the multicore optical fiber, the termination piece comprising a distal tip and located within the first substantially rigid portion opposite the flexible portion; and
a force sensing region integrated with the flexible portion and configured to enable determining of an axial force exerted on a distal end of the elongated outer body by sensing changes in curvature or strain on the multicore optical fiber resulting from buckling of the flexible portion in the force sensing region in response to the axial force,
wherein the shape sensing occurs along the multicore optical fiber to the tip of the termination piece.

16. An optical shape sensing device comprising:
an elongated outer body configured to maneuver through a passage, the elongated outer body comprising a proximal substantially rigid portion and a distal substantially rigid portion separated by a space;
a multicore optical fiber extending through the elongated outer body the multicore optical fiber enabling shape sensing by tracking positioning of the multicore optical fiber;
a termination piece attached to a distal tip of the multicore optical fiber, the termination piece comprising a distal tip and located within the distal substantially rigid portion; and
a force sensing region substantially coinciding with the space separating the proximal and distal substantially rigid portions, and configured to enable determining of an axial force exerted on a distal end of the elongated body by sensing an amount of torsion of the multicore optical fibers, wherein the proximal and distal substantially rigid portions are configured to rotate with respect to one another in response to the axial force being exerted on the distal end of the elongated body, the rotation causing the torsion of the multicore optical fibers,
wherein the shape sensing occurs along the multicore optical fiber to the tip of the termination piece.

17. The device of claim 16, wherein adhesive binds the multicore optical fiber to the proximal and distal substantially rigid portions of the elongated outer body.

18. An optical shape sensing device comprising:
an elongated outer body comprising flexible tubing configured to maneuver through a passage;
a multicore optical fiber extending through the elongated outer body, and enabling shape sensing by tracking positioning of the multicore optical fiber along a length of the multicore optical fiber;
a termination piece attached to a distal tip of the multicore optical fiber, the termination piece comprising a distal tip;
a compliant material located between a portion of the multicore optical fiber and an inner surface of a corresponding portion of the elongated outer body; and
a plurality of force sensing regions embedded in the compliant material, each force sensing region comprising a solid element, lateral forces exerted on the elongated outer body displacing at least one of the solid elements of the plurality of force sensing regions,
wherein an extent of the displacing senses the lateral forces, including lateral forces exerted on the termination piece, and
wherein the shape sensing occurs along the multicore optical fiber to the tip of the termination piece.

19. The device of claim 1, further comprising a processing unit, wherein the processing unit is programmed to measure changes in axial strain in a central optical core of the multicore optical fiber at the force sensing region, and to convert the measured axial strain changes to the amount of axial force, so as to determine said amount of axial force applied to the distal end of the elongated outer body is.

20. The device of claim 1, further comprising a processing unit, wherein the processing unit is programmed to measure torsion that occurs in additional optical cores, helically wrapped around a central optical core of the multicore optical fiber, and to convert the measured torsion to the amount of axial force, so as to determine said amount of axial force applied to the distal end of the elongated outer body.

21. An optical shape sensing device comprising:
an elongated outer body configured to maneuver through a passage, the elongated outer body comprising a flexible tubing and a substantially rigid tube connected to a distal end of the flexible tubing;
a disk attached to a distal inner tubing, which extends into a distal side of the substantially rigid tube a distal end of the elongated outer body, the disk being spaced apart from the distal end of the elongated body by a gap when in an uncompressed state;
a multicore optical fiber extending through the elongated outer body, the multicore optical fiber enabling shape sensing by tracking positioning of the multicore optical fiber;
a termination piece attached to a distal tip of the multicore optical fiber the termination piece comprising a distal tip and located within the distal inner tubing; and
a force sensing region substantially coinciding with an area between the distal inner tubing and additional inner tubing located at a proximal side of the rigid tube, and configured to enable determining of an axial force exerted on the disk sensing compression of at least the multicore optical fiber, wherein the gap closes in response to the axial force until the gap is in physical contact with the distal end of the elongated body, thereby stopping compression of the multicore optical fiber and of the termination piece, and
wherein the shape sensing occurs along the multicore optical fiber to the tip of the termination piece.

* * * * *